US00PP26128P3

(12) United States Plant Patent
Danziger

(10) Patent No.: US PP26,128 P3
(45) Date of Patent: Nov. 24, 2015

(54) ***DIANTHUS* PLANT NAMED 'DIANMAGENT'**

(50) Latin Name: *Dianthus plumarius*
Varietal Denomination: DIANMAGENT

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 37 days.

(21) Appl. No.: 13/987,201

(22) Filed: Jul. 9, 2013

(65) Prior Publication Data

US 2015/0020259 P1 Jan. 15, 2015

(51) Int. Cl.
*A01H 5/02* (2006.01)

(52) U.S. Cl.
USPC ..... Plt./282

(58) Field of Classification Search
USPC ..... Plt./282
CPC ..... A01H 5/0233
See application file for complete search history.

*Primary Examiner* — Keith O. Robinson
(74) *Attorney, Agent, or Firm* — Cassandra Bright

(57) ABSTRACT

A new and distinct *Dianthus* cultivar named 'DIANMAGENT' is disclosed, characterized by low maintenance, robust outdoor growth as well as hardy to USDA zone 5. The new variety is very floriferous and perpetual flowering. The new variety is a *Dianthus,* normally produced as an outdoor garden or container plant.

2 Drawing Sheets

Figure 1:
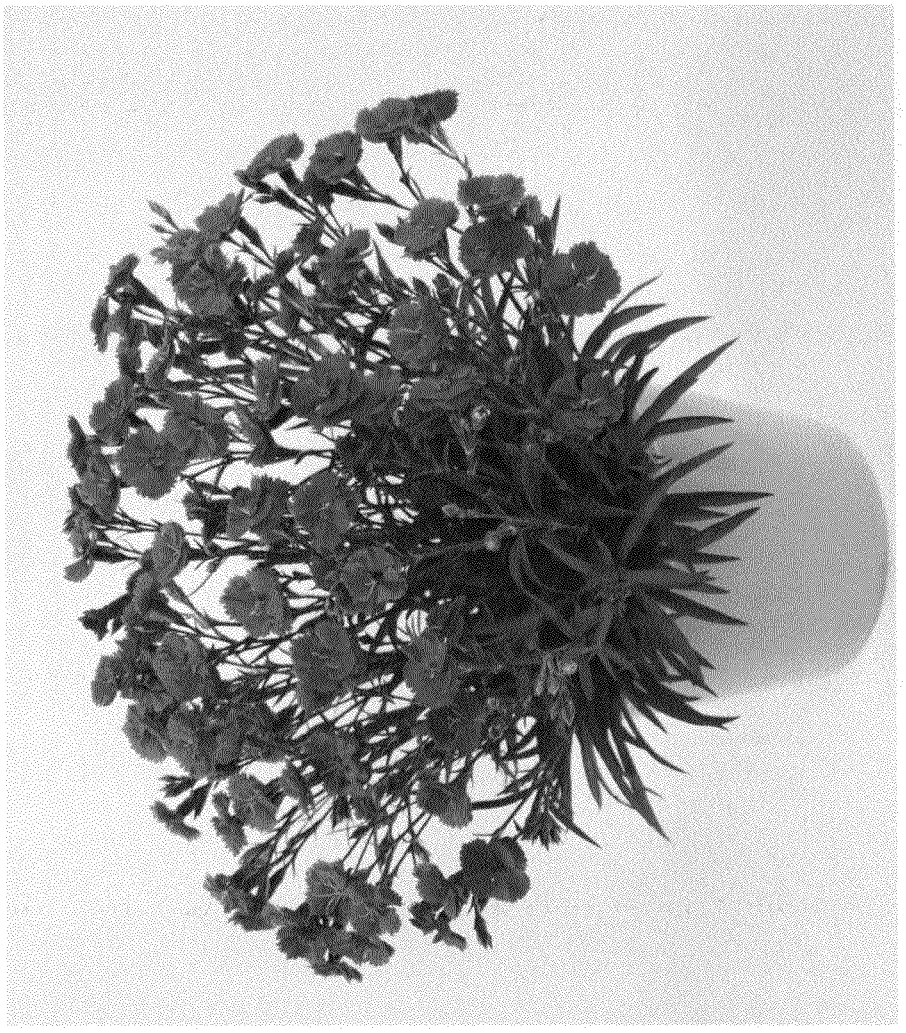

Latin name of the genus and species: *Dianthus plumarius.* Variety denomination 'DIANMAGENT'.

BACKGROUND OF THE INVENTION

The new *Dianthus* cultivar is a product of a planned breeding program conducted by the inventor, Gavriel Danziger, in Moshav Mishmar Hashiva, Israel. The objective of the breeding program was to produce new *Dianthus* varieties for ornamental commercial applications. The cross resulting in this new variety was made during October of 2009.

The seed parent is the unpatented, proprietary seedling variety referred to as *Dianthus plumarius* 'Acc. 1' The pollen parent is the unpatented, proprietary seedling variety referred to as *Dianthus plumarius* 'Acc. 9'. The new variety was discovered in November of 2010 by the inventor in a group of seedlings resulting from the 2009 crossing, in a research greenhouse in Moshav Mishmar Hashiva, Israel.

Asexual reproduction of the new cultivar was performed by vegetative tip cuttings. This was first performed at a research greenhouse in Moshav Mishmar Hashiva, Israel in December of 2010 and has shown that the unique features of this cultivar are stable and reproduced true to type in successive generations.

SUMMARY OF THE INVENTION

The cultivar 'DIANMAGENT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIANMAGENT' These characteristics in combination distinguish 'DIANMAGENT' as a new and distinct *Dianthus* cultivar:

1. Very floriferous.
2. Robust outdoor performance.
3. Low maintenance in garden situations.
4. Perpetual flowering.
5. Hardy to USDA zone 5

Plants of the new cultivar 'DIANMAGENT' are similar to plants of the seed parent, Dianthus plumarius 'Acc. 1' in most horticultural characteristics, however, plants of the new cultivar 'DIANMAGENT' is are much more floriferous than the seed parent. 'DIANMAGENT' also has a perpetual flowering habit whereas seed parent flowers only in the spring. Additionally, 'DIANMAGENT' has a more flexible growth, habit, leaves and stems are not as stiff as the seed parent.

Plants of the new cultivar 'DIANMAGENT' are similar to plants of the pollen parent; *Dianthus plumarius* 'Acc. 9' in most horticultural characteristics, however, plants of the new cultivar 'DIANMAGENT' is hardy to USDA zone 5, whereas the pollen parent is less resistant to low temperatures. 'DIANMAGENT' is more robust than the pollen parent; generally 'DIANMAGENT' is more suitable for a broad range of environmental conditions than the pollen parent. Also 'DIANMAGENT' produces smaller flowers that stand above the foliage; the pollen parent's flowering is larger and lower (partially hidden in the foliage).

COMMERCIAL COMPARISON

Plants of the new cultivar 'DIANMAGENT' are comparable to the unpatented, commercial *Dianthus* variety 'Gepo'. The two *Dianthus* varieties are similar in most horticultural characteristics; however, the new variety 'DIANMAGENT' produces a semi double, magenta colored flower, whereas comparator 'Gepo' produces a single form flower of dark lilac color. 'DIANMAGENT' also has a perpetual flowering habit, whereas comparator 'Gepo' flowers only in the spring. Additionally 'DIANMAGENT' is less compact in habit than comparator 'Gepo'.

Plants of the new cultivar 'DIANMAGENT' can also be compared to the unpatented, commercial *Dianthus* variety 'Kahori'. These varieties are similar in most horticultural characteristics; however 'DIANMAGENT' produces a semi double, magenta colored flower, whereas comparator 'Kahori' produces a single form flower of pink-lavender color. 'DIANMAGENT' is shorter in height; 20 cm compared to 35 cm of comparator 'Kahori'. Additionally 'DIANMAGENT' has good flower form (open petals) compared to incurved petals of comparator 'Kahori'.

BRIEF DESCRIPTION OF THE PHOTOGRAPHS

The accompanying photograph in FIG. 1 illustrates in full color a typical plant of 'DIANMAGENT' grown in a greenhouse, in a 5 inch pot. Age of the plant photographed is approximately 14 weeks from a rooted cutting.

Figure 2:
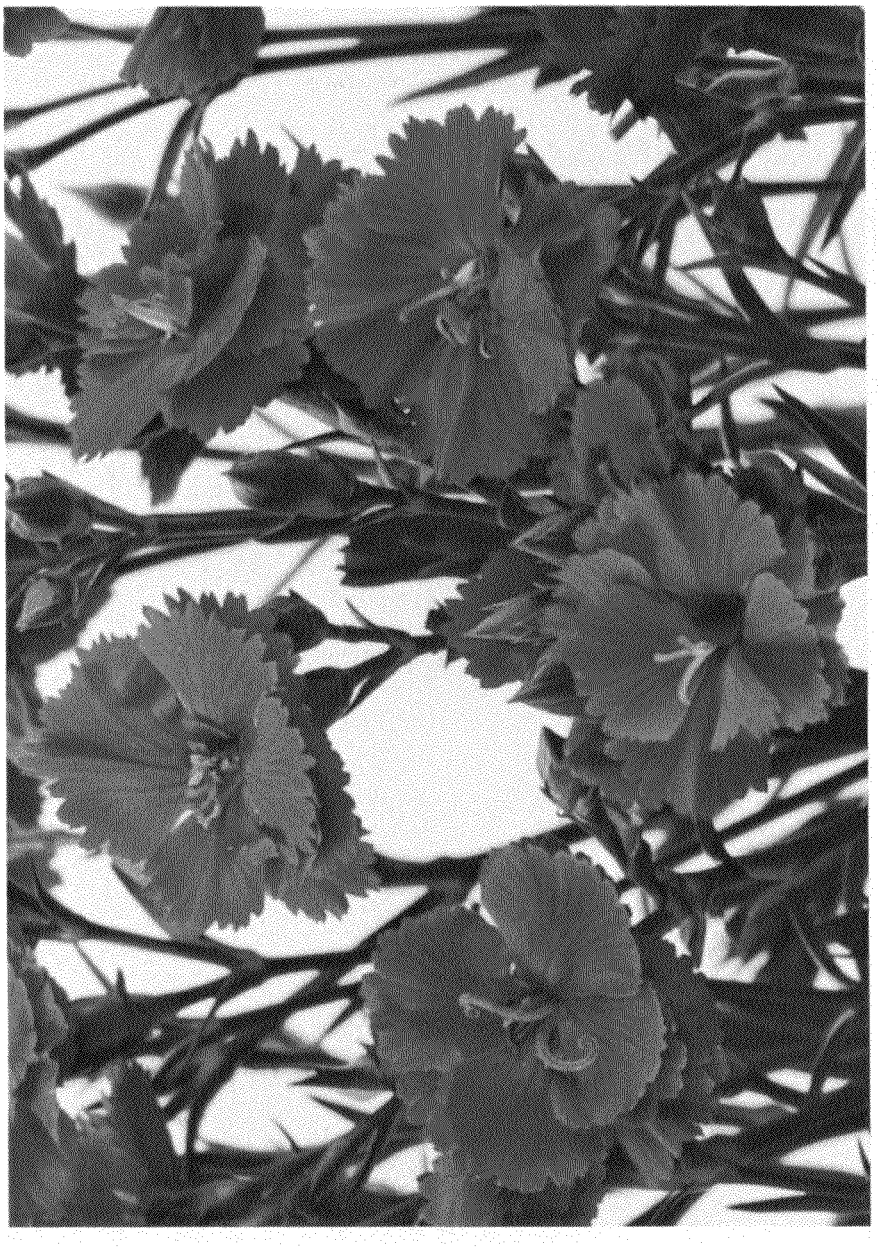

FIG. 2 illustrates in full color a close up of a typical bloom of 'DIANMAGENT'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DIANMAGENT' plants grown in a greenhouse during the Fall in Moshav Mishmar Hashiva, Israel. The growing temperature ranged from 18° C. to 25° C. during the day and from 8° C. to 12° C. during the night. General light conditions are bright, normal sunlight. Measurements and numerical values represent averages of typical plant types.

Botanical classification: *Dianthus plumarius* 'DIANMAGENT'.

PROPAGATION

Time to initiate roots: About 10 days at approximately 24° C.
Time to produce a rooted cutting: About 18 days at 24° C.
Root description: Fibrous roots, approximately 1 to 3 mm in diameter, colored near Orange-White 159C.

PLANT

Age of plant described: Approximately 14 weeks from rooted cutting.
Pot size: 5 inch.
Plant type: Medium compact, upright perennial.
Plant habit: Upright growing stems emerge basally.
Plant spread: Approximately 16 cm.
Height: Approximately 20 cm.
Growth rate: Planting to flower 10-12 weeks.
Length plant stem: Average 15 cm.
Diameter of plant stem: Approximately 0.5 cm.
Quantity stems: Approximately 5-6.
Stem:
- *Color*.—Near RHS group Greyed-Green 189A.
- *Texture*.—Smooth.

Internode length: Average 4 cm.

FOLIAGE

Leaf:
- *Arrangement*.—Opposite (in pairs).
- *Quantity*.—Approximately 4-6 per stem.
- *Average length*.—Approximately 7-8 cm.
- *Average width*.—Approximately 0.5 cm.
- *Shape of blade*.—Elongated.
- *Apex*.—Pointed.
- *Base*.—Square.
- *Attachment*.—Sessile.
- *Margin*.—Entire.
- *Texture of top surface*.—Smooth.
- *Texture of bottom surface*.—Smooth.
- *Pubescence*.—None.
- *Color*.—Young foliage upper side: Near RHS group Greyed-Green 189A. Young foliage under side: Near RHS group Greyed-Green 189A. Mature foliage upper side: Near RHS group Greyed-Green 189A. Mature foliage under side: Near RHS group Greyed-Green 189A.
- *Venation*.—Type: One central. Venation color upper side: Near RHS group Greyed-Green 189A. Venation color under side: Near RHS group Greyed-Green 189A.

FLOWER

Natural flowering season: Perpetual flowering.
Inflorescence type and habit: Branching and upright.
Flower longevity on plant: 2-3 weeks.
Quantity of flowers: Approximately 50 flowers on a 14 week old plant.
Flowers persistent or self cleaning: Persistent shrinking.
Fragrance: Mild.
Inflorescence size:
- *Diameter*.—Approximately 4 cm.
- *Height*.—Approximately 20 cm.

Individual flower size:
- *Diameter*.—Approximately 2.5cm.
- *Length*.—Approximately 2-2.25cm.

Petals, excluding tube:
- *Petal arrangement*.—Inconcentric whorls.
- *Shape*.—Deltoid.
- *Base*.—Attenuate and folded inward.
- *Margin*.—Mildly serrated.
- *Apex*.—Blunt & rounded.
- *Length*.—2.5 cm.
- *Width*.—1.0 cm.
- *Petal quantity*.—24.
- *Texture*.—Smooth.
- *Aspect*.—Upright and bending outward.

Color:
- *When opening*.—Upper surface: Near RHS group Red-Purple 61B. Lower surface: Near RHS group Red-Purple 68A.
- *Fully opened*.—Upper surface: Near RHS group Red-Purple 61B. Lower surface: Near RHS group Red-Purple 68A.
- *Fading*.—Upper surface: Near RHS group Red-Purple 71A. Lower surface: Near RHS group Red-Purple 70C.

Tube:

*General description*.—Tube consists of the elongated, unfused base of the petals. Tube shape caused by a fused calyx. Length: 1.5cm. Width: 0.5 cm. Texture: Smooth.

Color:

*When opening*.—Upper surface: Near RHS group Greyed-Green 189A. Lower surface: Near RHS group Greyed-Green 189A.

*Fully opened*.—Upper surface: Near RHS group Greyed-Green 189A. Lower surface: Near RHS group Greyed-Green 189A.

*Fading*.—Upper surface: No fading. Lower surface: No fading.

Bud:

*Shape*.—Elongated cylinder.

*Length*.—Average 2 cm.

*Diameter*.—Average 0.6 cm.

*Color*.—Near RHS group Greyed-Green 189A.

Sepals:

*Quantity*.—5.

*Arrangement*.—Single overlapping whorl.

*Shape*.—Elongated and pointed at end.

*Length*.—Approximately 1.5 cm.

*Width*.—Approximately 0.3 cm.

*Calyx diameter*.—Approximately 0.4 cm.

*Margin*.—Smooth.

*Apex*.—Pointed.

*Texture*.—Smooth upper and lower surfaces.

*Color*.—Near RHS group Greyed-Green 189A upper and lower surfaces.

Bracteoles:

*Shape*.—Identical to sepals but shorter.

*Quantity per flower*.—4.

*Length*.—Approximately 0.5 cm.

*Width*.—Approximately 0.3 cm.

*Margin*.—Smooth.

*Texture*.—Smooth.

*Color*.—Near RHS group Greyed-Green 189A.

Peduncle:

*Length*.—Average 10 cm.

*Diameter*.—0.25 cm.

*Color*.—Near RHS group Greyed-Green 189A.

*Orientation*.—Upright.

*Strength*.—Rigid.

*Texture*.—Smooth.

Pedicel:

*Length*.—Average 5 cm.

*Diameter*.—0.1 cm.

*Color*.—Near RHS group Greyed-Green 189A.

*Orientation*.—Upright.

*Strength*.—Flexible, elastic.

REPRODUCTIVE ORGANS

Stamens:

*Number*.—Varies according to season, most poorly developed.

*Filament length*.—Approximately 0.5 cm.

Anthers:

*Shape*.—Oblong when well developed.

*Length*.—Approximately 0.2 cm.

*Color*.—Near RHS group Black 202C.

*Pollen*.—Viable.

Pistil:

*Number*.—2-4.

*Length*.—Approximately 2.3 cm.

*Style*.—Length: Approximately 1.5 cm. Color: Near RHS group Red-Purple 69B.

Stigma:

*Shape*.—Tubular and bending.

*Color*.—Near RHS group Red-Purple 69B.

*Ovary shape*.—Oblong.

*Ovary diameter*.—0.3 cm.

*Ovary length*.—0.9 cm.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani,* Typical pests include; various species of *Thysanopthera,* various *Aphis* species, and various species of *Tetranychus.*

Temperature tolerance: USDA zone 5 tolerant.

What is claimed is:

1. A new and distinct cultivar of *Dianthus* plant named 'DIANMAGENT' as herein illustrated and described.

* * * * *